United States Patent [19]
Goldman et al.

[11] Patent Number: 5,591,399
[45] Date of Patent: Jan. 7, 1997

[54] SYSTEM FOR DIAGNOSING OXYGENATOR FAILURE

[76] Inventors: Julian M. Goldman, 130 S. Hudson St., Denver, Colo. 80222; Lyle Kirson, 3405 E. Eastman, Denver, Colo. 80210

[21] Appl. No.: 483,953

[22] Filed: Jun. 7, 1995

Related U.S. Application Data

[63] Continuation of Ser. No. 137,570, Oct. 14, 1993, abandoned.
[51] Int. Cl.⁶ .................................................. A61M 1/14
[52] U.S. Cl. .................. 422/44; 422/45; 604/4; 604/6; 604/31; 604/50; 128/DIG. 3
[58] Field of Search .............................. 604/4, 6, 31, 50; 128/DIG. 3; 422/44, 45

[56] References Cited

U.S. PATENT DOCUMENTS

| | | | |
|---|---|---|---|
| 4,401,431 | 8/1983 | Arp | 604/4 |
| 4,598,733 | 7/1986 | Kanno et al. | 137/406 |
| 4,650,457 | 3/1987 | Morioka et al. | 604/4 |
| 5,158,534 | 10/1992 | Berry et al. | 604/4 |

*Primary Examiner*—Nina Bhat
*Attorney, Agent, or Firm*—Baker, Maxham, Jester & Meador

[57] ABSTRACT

A system which provides information necessary to diagnose a failure or malfunction of an oxygenator. The system provides information to differentiate oxygenator failure from other causes of hypoxemia (inadequate blood oxygen concentration). Such as malfunction of the ventilating circuit, or components of the ventilating circuit. This is accomplished by analyzing the oxygen concentration of the ventilating gas entering the oxygenator, the flow of the ventilating gas entering the oxygenator, and also the pressure in the ventilating gas circuit or the pressure of gas within the oxygenator. As a result the invention provides information to diagnose ventilating gas flow obstruction or a gas leak from an oxygenator housing.

17 Claims, 11 Drawing Sheets

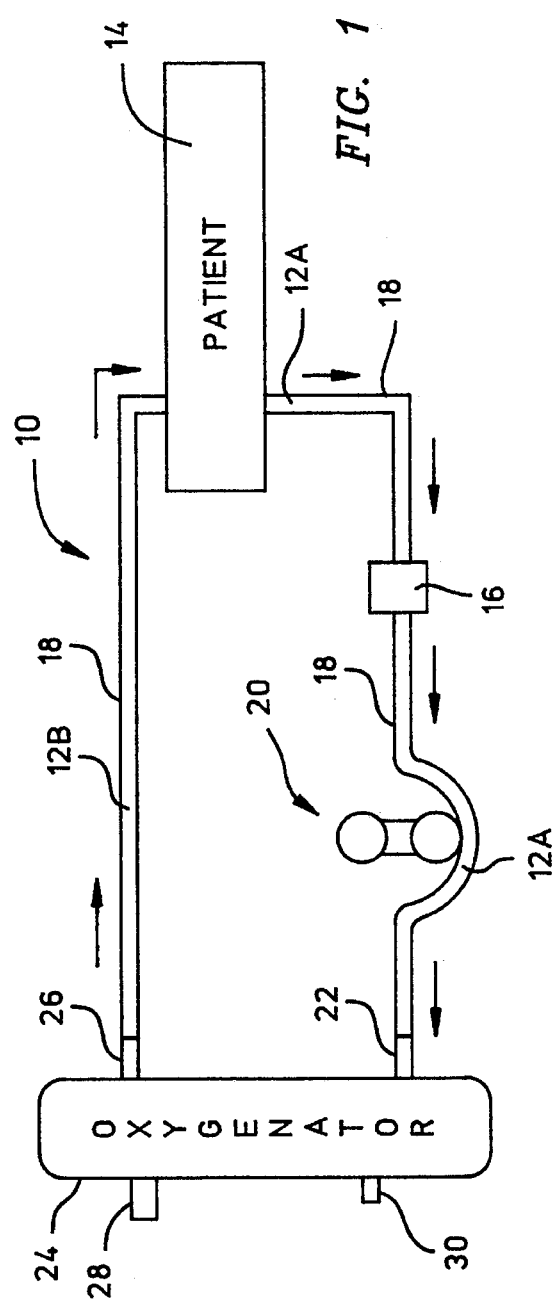
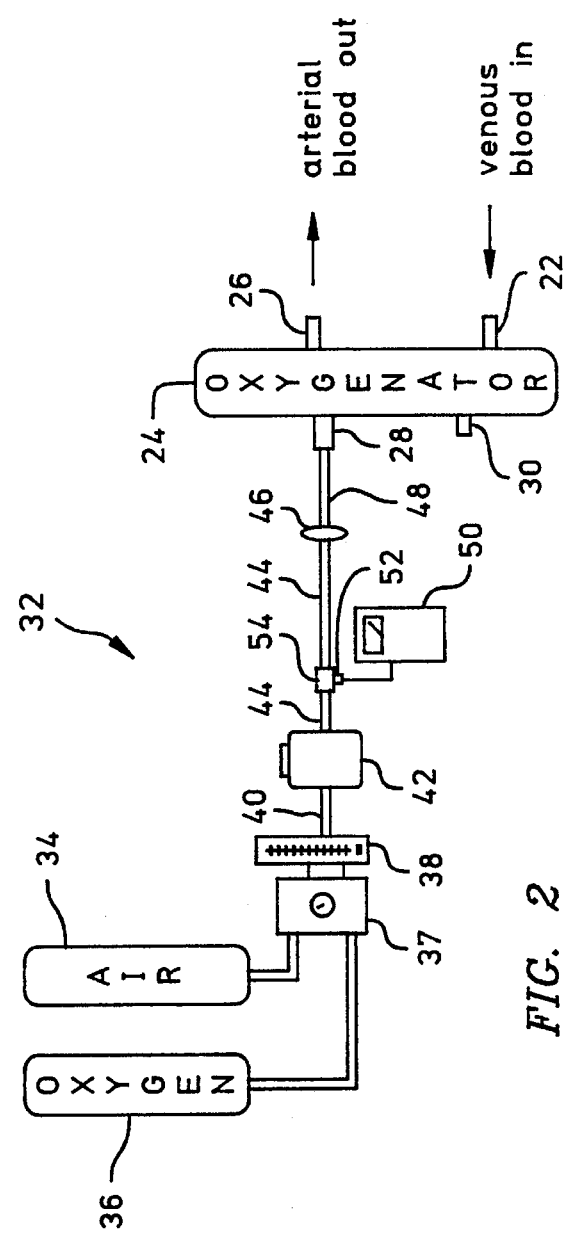
FIG. 1
FIG. 2

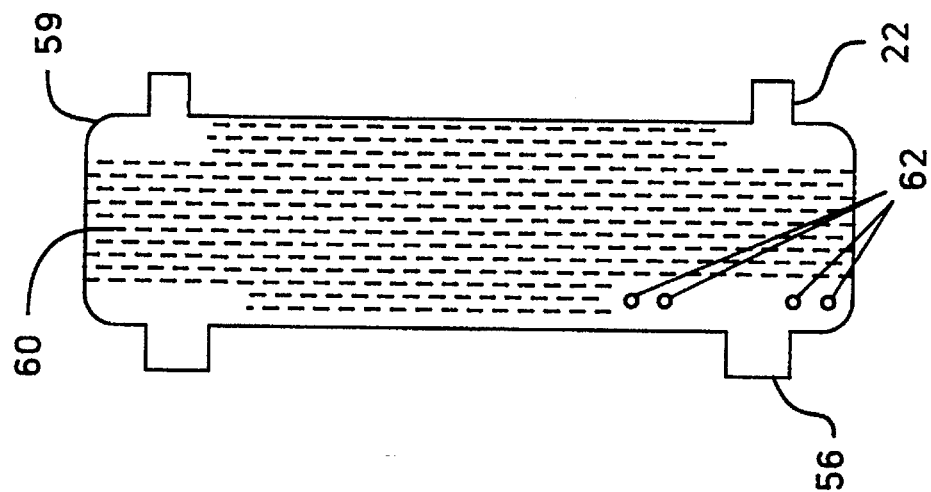
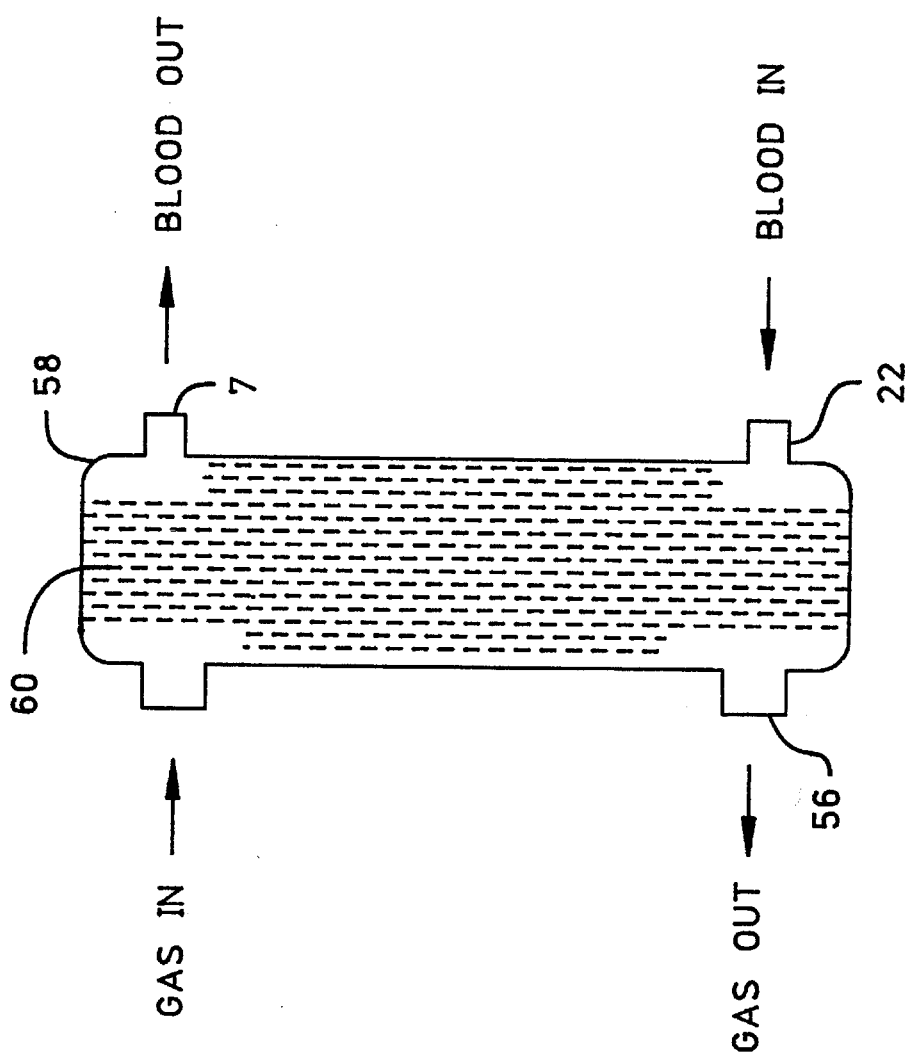

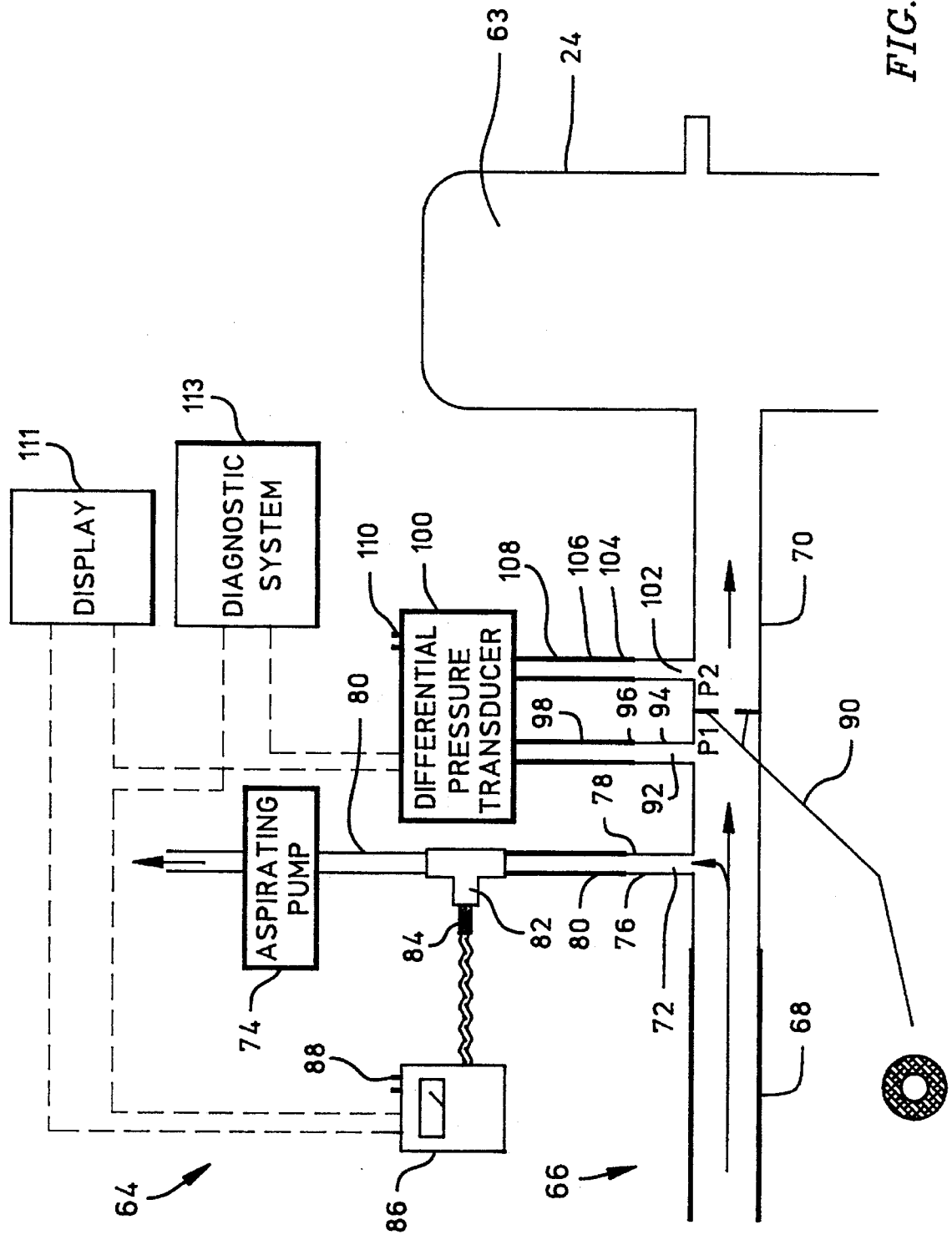

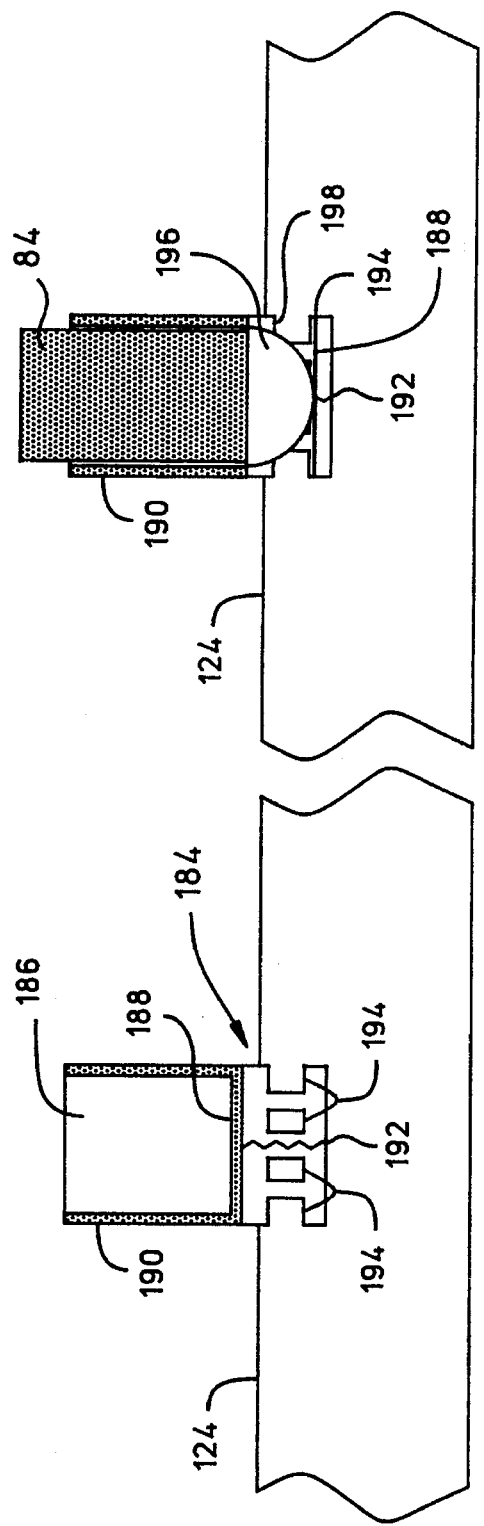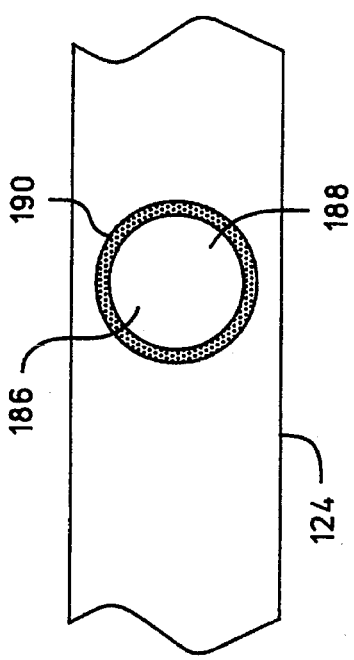

Fault Diagnosis Matrix for Oxygenator Ventilating Gas Supply

| Fault | Sensor | | |
|---|---|---|---|
| | "Passive" Oxygen Sensor | "Aspirating" Oxygen Sensor | Flow (pneumotachography) |
| Low O₂ Concentration (without cessation of flow) | ✓ | | |
| Disconnection (at any point in circuit) | | ✓ | ✓ |
| Leak | | ✓ | ✓ |
| Excessive Flow | | | ✓ |

SYSTEM FOR DIAGNOSING OXYGENATOR FAILURE

CROSS REFERENCE TO RELATED APPLICATION

This is a continuation of United States patent application Ser. No. 08/137,570, filed Oct. 14, 1993, now abandoned.

BACKGROUND OF THE INVENTION

1. Field of Invention

This invention relates to a system for the evaluation of oxygenator function, and in particular to a system for differentiating oxygenator malfunction from other causes of inadequate gas exchange by an oxygenator.

2. Discussion

A. A Description of Cardiopulmonary Bypass

Cardiopulmonary bypass (bypassing the heart and lungs) refers to the procedure of removing blood from the venous side of a patient's circulation and returning that blood to the arterial side of the circulation (usually to the aorta). During cardiopulmonary bypass, it is necessary to artificially perform the function of the patient's heart and lungs in order to maintain the health and life of the patient. It is the role of the oxygenator, or artificial lung, to perform the function of the lungs.

FIG. 1 is a schematic representation of the design of that part of a cardiopulmonary bypass circuit 10 performing the functions of blood removal, gas exchange and blood return. Venous blood 12A is continuously siphoned from the patient's body 14, usually from the right atrium of the heart, to a venous reservoir 16 via clear polyvinyl chloride tubing 18. This venous blood, which is low in oxygen content and high in carbon dioxide content, is subsequently pumped by a blood pump 20 through a venous blood inlet 22 of an oxygenator 24 and into a gas exchange compartment (not shown) of the oxygenator 24. After perfusing the gas exchange compartment, the blood 12B which is now oxygenated, exits the oxygenator 24 via an arterial blood outlet 26 and returns to the patient. Gas exchange occurs inside the gas exchange compartment of the oxygenator 24 such that the blood 12B returned to the patient has had oxygen added and carbon dioxide removed. The arrows in FIG. 1 represent the direction of blood flow.

Simultaneously with the delivery of blood to the oxygenator, a mixture of medical grade air and oxygen is delivered via an oxygenator ventilating circuit to a gas inlet 28 of the oxygenator 24. This gas ventilates the oxygenator (flows through the oxygenator) in a manner analogous to that which occurs in the human lung. That is, within the gas exchange compartment (not shown) of the oxygenator 24 oxygen from the ventilating gas diffuses into the blood perfusing the oxygenator 24, while carbon dioxide leaves the blood and enters the ventilating gas. The ventilating gas, now high in carbon dioxide content and lower in oxygen content, exits the oxygenator through a gas outlet 30. Generally, the concentration of oxygen in the patient's blood will be closely dependent upon the concentration of oxygen perfusing the oxygenator 24, and the concentration of carbon dioxide in the patient's blood will be closely dependent upon the total gas flow perfusing the oxygenator.

A representative design of a typical oxygenator ventilating circuit 32 (a circuit that delivers gas to an oxygenator) for cardiopulmonary bypass is shown in FIG. 2. Air 34 and oxygen 36 are delivered, under pressure, to the oxygenator ventilating circuit 32. The gases are usually piped in from the hospital's central gas supply, but can be delivered from gas tanks. The two gases then enter a blender 37 which reduces pressure, and proportions the gases to achieve the concentration designated by the perfusionist (the individual who operates the cardiopulmonary bypass machine). The blended gas then enters a flow controller 38 which allows the perfusionist to set the flow, in liters per minute, of gas to be delivered into the remainder of the ventilating circuit 32. From the flow controller 38, tubing 40 carries the gas to an anesthetic vaporizer 42 where a volatile anesthetic can be added to the gas flow. From the vaporizer 42, additional tubing 44 carries the gas mixture to a bacterial filter 46 and then on to the oxygenator 24. The gas mixture enters the oxygenator 24 through its gas inlet 28. The conduit for the gas, from flow controller 38 to oxygenator 24, is normally 0.25 inch clear, flexible polyvinyl chloride tubing 40, 44 and 48. Frequently, an oxygen analyzer 50 is placed in the ventilating circuit to assure that the gas exiting the blender 37 (and assumed to be flowing into the oxygenator 24) has the oxygen concentration designated by the perfusionist. A sensor portion 52 of the oxygen analyzer 50 is inserted into an adapter 54 which is usually positioned in the ventilating circuit prior to the bacterial filter 46.

Oxygenators in clinical use today are of two types. Bubble oxygenators are designed so that ventilating gas is bubbled directly through a reservoir of blood. Before the blood is returned to the patient, the bubbles are removed. Membrane oxygenators are designed to always keep the blood and ventilating gas separate. The membrane acts as a barrier which allows for exchange of gas molecules, but prevents the entry of gas bubbles into the blood.

B. The Causes of Hypoxemia

Various events occur during cardiopulmonary bypass which affect the concentration of oxygen and carbon dioxide present in the patient's blood. If the blood concentration of either of these gases varies from normal physiologic levels for even a short period of time, serious and permanent harm can result. The degree of harm will vary with the degree of insult, however, variations in the blood concentration of either gas for a short duration can result in permanent brain and neurologic damage, or even death. It is primarily the responsibility of the perfusionist, along with other members of the surgical team, to assure that the blood concentration of oxygen and carbon dioxide do not vary from normal physiologic levels during cardiopulmonary bypass.

Among the events that can alter the concentration of oxygen or carbon dioxide circulating in the patient's blood during cardiopulmonary bypass is a problem with the oxygenator. Such problems can be the result of an equipment malfunction or an operator error, both referred to henceforth as a malfunction. When a malfunction occurs, it is frequently not recognized until some resultant physiologic event, such as hypoxemia (an inadequate blood oxygen concentration), becomes evident. At that point in time, the cause of the problem still needs to be ascertained, and corrective measures taken quickly to insure the safety of the patient.

An oxygenator malfunction can involve, but is not necessarily limited to any of the following events, all of which compromise the oxygenator's ability to perform adequate gas exchange:

(1) a leak in the membrane (in a membrane oxygenator) allowing blood to enter the gas side of the gas exchange compartment;

(2) blood clot formation on the membrane;

(3) a crack in the oxygenator housing allowing gas to escape (to the atmosphere) before complete gas exchange occurs;

(4) obstruction of gas flow into or through the gas exchange compartment; and (5) obstruction of gas flow out of the oxygenator gas exchange compartment, dangerously increasing the gas pressure within the gas exchange compartment. Hypoxemia can also occur despite a correctly functioning oxygenator due to other malfunctions which result in inadequate gas exchange by the oxygenator. These may involve unrecognized problems (unplanned alteration) with either the oxygen concentration or the flow of gas delivered to, and entering, the oxygenator. Gas supply malfunctions which can compromise attaining normal blood concentrations of oxygen and carbon dioxide include:

(1) oxygen concentration alteration secondary to a gas supply (34 and 36) malfunction 37, blender malfunction, or similar event;

(2) loss or absence of total gas flow secondary to an event such as disconnection of the tubing at any point of ventilating circuit 32;

(3) reduced gas flow secondary to a leak at any period in the ventilating circuit 32; and (4) excessive gas flow from a blender 37 or flow controller 38 malfunction.

Additionally, the present inventor has discovered that a Venturi effect can result from a small break in the gas supply line 40, 44 and 48. This effect entrains room air into the oxygenator ventilating circuit 32, resulting in both excessive gas flow and a decrease in delivered oxygen concentration of said gas flow to the oxygenator secondary to room air dilution of the ventilating gas. Entrainment of room air into the ventilating gas is a previously unrecognized problem which can impair oxygenation of the patient. This problem of room air entrainment would be very difficult (and perhaps impossible) to detect by manual and/or visual inspection.

The frequency of oxygenator malfunctions is difficult to estimate for several reasons. First, because of the present inability to accurately monitor oxygenator function, events occur which are never recognized or accurately diagnosed. The present inventor has been informed by a representative of a major oxygenator manufacturer that of all oxygenators returned to the manufacturer for investigation of an intraoperative malfunction, only 30% are defective: The other 70% are free of defects. One can conclude therefore that those defect-free oxygenators were returned to the manufacturer because a problem other than oxygenator failure was misdiagnosed as a defective oxygenator.

Second, there is reticence on the part of practitioners to report untoward events and many experts in the field of cardiopulmonary bypass agree that numerous untoward events go unreported. (See Pierce, E., "Are Oxygenators (airplanes, oil spills, pesticides) Safe?", *Ann. Thorac. Surg.* 1989;48:467–468; Kurusz, M. et al., "Risk Containment During Cardiopulmonary Bypass", *Sem. Thor. Cardiovasc Surg.* 1990;2:400–409; Belcher, P., et al., "Hypoxemia During Cardiopulmonary Bypass", *Ann. Thorac. Surg.*, 1990;50:336.) In spite of this, there are many published reports that demonstrate that the scenarios listed above are true problems, and not merely theoretical. (See Groom, R., "Do You Use A Gas Supply Oxygen Analyzer?", *AACP Newsletter,* 1991;7; Rubsamen, D., "Continuous Blood Gas Monitoring During Cardiopulmonary Bypass-How Soon Will It Be The Standard Of Care?", *J. Cardiothor. Anesth.,* 1990;4:1–4, Kurusz, M., et al., "Perfusion Accident Survey", *Proceedings of Am. Ac. of CV Perf.,* 1986;7:57–65; Ditchik, J., et al., "Can we do without $O_2$ analyzers?", *Anesthesiology,* 1984;61:629–30; McGarrigle, R., "General Anesthesia Without $O_2$ Analyzer-A Substandard Practice.", *Anesthesiology,* 1985;63:116; Ghanooni, S., et al., "A Case Report Of An Unusual Disconnection.", *Anesth. Analg.,* 1983;62:696-7; Dorsch, S. et al., "Use Of Oxygen Analyzers Should Be Mandatory.", *Anesthesiology,* 1983;59:161-2; Robblee, J., et al., "Hypoxemia After Intraluminal Oxygen Line Obstruction During Cardiopulmonary Bypass.", *Ann. Thorac. Surg.,* 1989;48:575-6; Gravlee, G., et al., "Hypoxemia During Cardiopulmonary Bypass From Leaks In The Gas Supply System.", *Anesth. Analg.,* 1985;64:649-50; Romanoff, M., et al., "Severe Hypocapnia During Cardiopulmonary Bypass.", Anesth. Analg., 1991; 72:410–11; Kubiak, D., et al., "Unusual Life-Threatening Hypercarbia During Cardiac Anesthesia And Cardiopulmonary Bypass.", *J. Cardiotho. Anesth..,* 1992;6:73–75; Maltry, D., et al., "Isofiurane-Induced Failure Of The Bentley-10 Oxygenator.", *Anesthesiology,* 1987;66:100–101; Cooper, S., et al., "Near Catastrophic Oxygenator Failure.", *Anesthesiology,* 1987;66:101–102; Dickinson, T., "Hypoxemia After Intraluminal Oxygen Line Obstruction During Cardiopulmonary Bypass.", *Ann. Thorac. Surg.,* 1990:512–513; Kurusz, M., et al., "Oxygenator Failure", *Ann. Thorac. Surg.,* 1990;49:511–513; Peirce II, E., "Are Oxygenators (airplanes, oil spills, pesticides) safe?", *Ann. Thorac. Surg.,* 1989;48:467–468; Warren, S., et al., "Severe Hypoxemia During Cardiopulmonary Bypass.", *Anaesthesia,* 1986;41:1266–1267.)

The lack of ability to diagnose an oxygenator failure is disturbing to the clinician. Replacing an oxygenator during cardiopulmonary bypass is a difficult and dangerous maneuver in itself, and if the cause of poor oxygenation is due to an occult defect in the ventilating gas delivery circuit and not to a defective oxygenator, valuable time is wasted "changing out" the oxygenator unnecessarily. In such a situation, after the oxygenator exchange is completed, the patient remains hypoxemic and the true etiology of the problem is yet to be determined.

During cardiopulmonary bypass, the concentrations of both oxygen and carbon dioxide of blood entering 12A and leaving 12B the oxygenator (venous entering, arterial leaving) are routinely monitored. This monitoring can be performed either through intermittent sampling of arterial and venous blood samples with analysis of these samples performed on a standard blood gas machine, or with the use of an in-line continuous monitor such as CDI Extracorporeal Blood Gas Monitoring System manufactured by 3M Corporation. Therefore, the perfusionist knows how much oxygen is being taken up by blood (and how much carbon dioxide is being released by this blood) as the blood perfuses the oxygenator. Inadequate uptake of oxygen by the blood perfusing the oxygenator, or inadequate (or excessive) removal of carbon dioxide from this blood perfusing the oxygenator, indicates either 1) a malfunction of the oxygenator, or 2) a problem with gas delivery to the oxygenator. Unfortunately there is currently no device or technique that differentiates between these two problems. That is, there is no device presently available for differentiating oxygenator failure from a gas delivery problem.

The only monitoring device available to clinicians for monitoring gas delivery to the oxygenator is a standard oxygen analyzer which, as described previously, is usually positioned in the oxygenator ventilating circuit prior to the bacterial filter (See FIG. 2, 50). Importantly, an oxygen analyzer, regardless of where it is positioned in the gas delivery circuit, is incapable of detecting oxygenator malfunction, a total loss or absence of gas flow, reduced gas flow secondary to a leak in the circuit, or excessive gas flow. The oxygen analyzer is only capable of detecting an unplanned oxygen concentration change such as might be caused by a malfunction of the central gas supply 34 and 36 of the hospital, malfunctioning blender 37, or misadjusted blender 37, as long gas is flowing. If the malfunction involves cessation of gas flow into the oxygenator, as might occur from an accidental disconnection at any point in the ventilating circuit 40, 44 and 48, the oxygen analyzer is incapable of detecting this problem and, in fact, will indicate the oxygen concentration of the gas in that segment of the ventilating circuit where the oxygen sensor is positioned (although no gas is entering the oxygenator). Furthermore, if entrainment of room air (Venturi effect) occurs at a point in the circuit beyond the position of the oxygen analyzer sensor, the oxygen analyzer will not be able to detect the decrease in oxygen concentration of the gas (nor the associated excessive gas flow) being delivered to the oxygenator.

A flow controller (See FIG. 2, 38) positioned at any point in the gas delivery circuit merely establishes flow into the circuit immediately past the point of its position. It does not monitor flow beyond that position. Moreover, a flow controller does not monitor or guarantee appropriate gas delivery into the oxygenator and is incapable of detecting a disconnection of the ventilating circuit, a leak in the ventilating circuit, entrainment of room air through a defect in any component of the ventilating circuit, or oxygenator malfunction.

In summary, 1) oxygenator malfunctions and 2) malfunctions of the ventilating gas delivery circuit have been documented. Despite the published and unpublished knowledge of these events, and the long-appreciated need to assure appropriate oxygenator function, (See American Society of Extra-Corporeal Technology. "Suggested Pre-Bypass Perfusion Checklist," *Perfusion Life,* 7:17, 1990 and reprinted in *Perfusion Life,* 10:36, 1993) the present inventor is aware of no device, mechanism, technique, or system that has been presented or invented which can differentiate oxygenator malfunction from these other causes of hypoxemia. This lack of diagnostic capabilities for isolation of an oxygenator malfunction has resulted in extended and tragic delays in correction of that problem.

Thus it would be desirable to provide a system for isolating oxygenator malfunctions. In particular it would be desirable to provide a system which can differentiate oxygenator malfunction from other causes of hypoxemia thereby prevent the dangerous maneuver of unnecessary oxygenator exchange.

C. Oxygenator Pressure Abnormalities

FIG. 3A shows the gas outlet 56 of one type of membrane oxygenator 58 which provides the sole outlet for gas exiting the oxygenator membrane compartment 60. FIG. 3B shows another oxygenator 59 design having multiple concealed openings 62 which vent to the atmosphere (in addition to gas outlet 56). The oxygenator in FIG. 3A has certain advantages, but also some disadvantages.

In an oxygenator 58 designed with a single outlet for gas exiting the membrane compartment 60, positive pressure can develop on the gas side of the oxygenator membrane (not shown) if an occlusion of the gas outlet 56 occurs. If the pressure on the gas side of the membrane exceeds the pressure on the blood side of the membrane, gas is forced through the membrane and into the arterial blood where it may form bubbles. This condition can result in the patient receiving an air embolism, which can result in stroke, heart attack or other organ damage.

Conversely, if a negative pressure develops on the gas side of the membrane (which can develop with a malfunction of the exhaust gas evacuation system which is usually connected to gas outlet 56), gas would be sucked through the oxygenator and inadequate gas exchange would occur. (See Mushlin, P., et al., "Inadvertent Development Of Subatmospheric Airway Pressure During Cardiopulmonary Bypass", *Anesthesiology,* 1989;71:459–462.) This would result in hypoxemia.

Aware of the potential danger of a buildup in gas pressure, the American Society of Extra-Corporeal Technology recommends an inspection to assure that the gas exhaust pathway is unobstructed. (See American Society of Extra-Corporeal Technology, "Suggested Pre-Bypass Perfusion Checklist", *Perfusion Life,* 7:17, 1990 and reprinted in *Perfusion Life.,* 10:36, 1993.) Thus it would be desirable to provide a system which can monitor the pressure in the gas compartment (the gas side of the membrane) of a membrane oxygenator.

SUMMARY OF THE INVENTION

The present invention makes use of the previously unappreciated fact that to differentiate oxygenator failure from a ventilating gas supply problem, both the oxygen concentration of the ventilating gas and the flow of the ventilating gas at the gas inlet of the oxygenator must be known. In the present invention the diagnosis of oxygenator failure is made through the process of exclusion, that is, by eliminating the existence of other causes of inadequate gas exchange within the oxygenator. In order to accomplish this goal, both the 1) oxygen concentration of the ventilating gas entering the oxygenator and 2) flow of ventilating gas entering the oxygenator are monitored. In addition, this invention can diagnose oxygenator failure by monitoring the pressure in the gas delivery circuit to an oxygenator, and/or monitoring the pressure on the gas side of the membrane in a membrane oxygenator.

In accordance with one aspect of the present invention a system for assessing oxygenator function is provided. The oxygenator receives and oxygenates a patient's blood and the system for assessing oxygenator function includes an oxygenator ventilating circuit means for supplying ventilating gas to the oxygenator. Also, an oxygen concentration measurement means measures the oxygen concentration of the ventilating gas supplied to the oxygenator. Also, a unit for measuring the flow of the ventilating gas supplied to the oxygenator is provided. Therefore the present invention provides the information necessary to diagnose a malfunctioning oxygenator by measuring the following three parameters:

A. Continuous, real-time analysis of the oxygen concentration of the gas entering the oxygenator.

B. Continuous, real-time analysis of the flow of gas entering the oxygenator.

Therefore, A+B provide a warning of:
1. a lack of adequate gas flow into the oxygenator;
2. a loss of total gas flow into the oxygenator;
3. inadequate delivery of gas flow to the oxygenator secondary to a leak in the gas delivery circuit;
4. excessive gas flow to the oxygenator; and
5. entrainment of room air into the gas delivery circuit (by comparison of the flow and oxygen concentration of the gas entering the oxygenator to the flow and oxygen concentration set by the perfusionist at the flow controller and gas blender, respectively).

C. Continuous, real-time analysis of the pressure on the gas side of the membrane (in a membrane oxygenator), thereby providing a warning of:

1. an increase in pressure in the gas delivery circuit;
2. a decrease in pressure in the gas delivery circuit; and
3. an increase in pressure on the gas side of the membrane in a membrane oxygenator.
4. a decrease in pressure on the gas side of the membrane in a membrane oxygenator.

BRIEF DESCRIPTION OF THE DRAWINGS

The various advantages of the present invention will become apparent to one skilled in the art by reading the following specification and by reference to the following drawings in which:

FIG. 1 is a schematic representation of the perfusion side of the cardiopulmonary bypass circuit.

FIG. 2 is a schematic representation of the ventilation side of the cardiopulmonary bypass circuit, specifically, the ventilating gas supply circuit.

FIG. 3A is a schematic representations of one type of membrane oxygenators having a single gas outlet.

FIG. 3B is a schematic representation of a membrane oxygenator having a primary gas outlet with multiple secondary smaller outlets.

FIG. 4 shows a cross-sectional view of the gas inlet and oxygenator of one embodiment of the invention in which the gas inlet of an oxygenator has been modified with the addition of three orifices and connectors, and an aspirating pump is used to sample gas for oxygen analysis.

FIGS. 11A–C represent an orifice with a one-way valve for positioning of the oxygen analyzer sensor in the modified gas inlet or oxygenator housing as described FIGS. 6 and 8. In particular, FIG. 11A shows a cross-sectional view of the valve without the oxygen analyzer sensor in place; FIG. 11B shows a cross-sectional view of the valve with the oxygen analyzer sensor inserted; and FIG. 11C shows top view of the valve without the oxygen analyzer sensor in place.

FIG. 12 shows a fault diagnosis matrix for ventilating gas supplied to the oxygenator.

DESCRIPTION OF THE PREFERRED EMBODIMENTS

Figure 5:
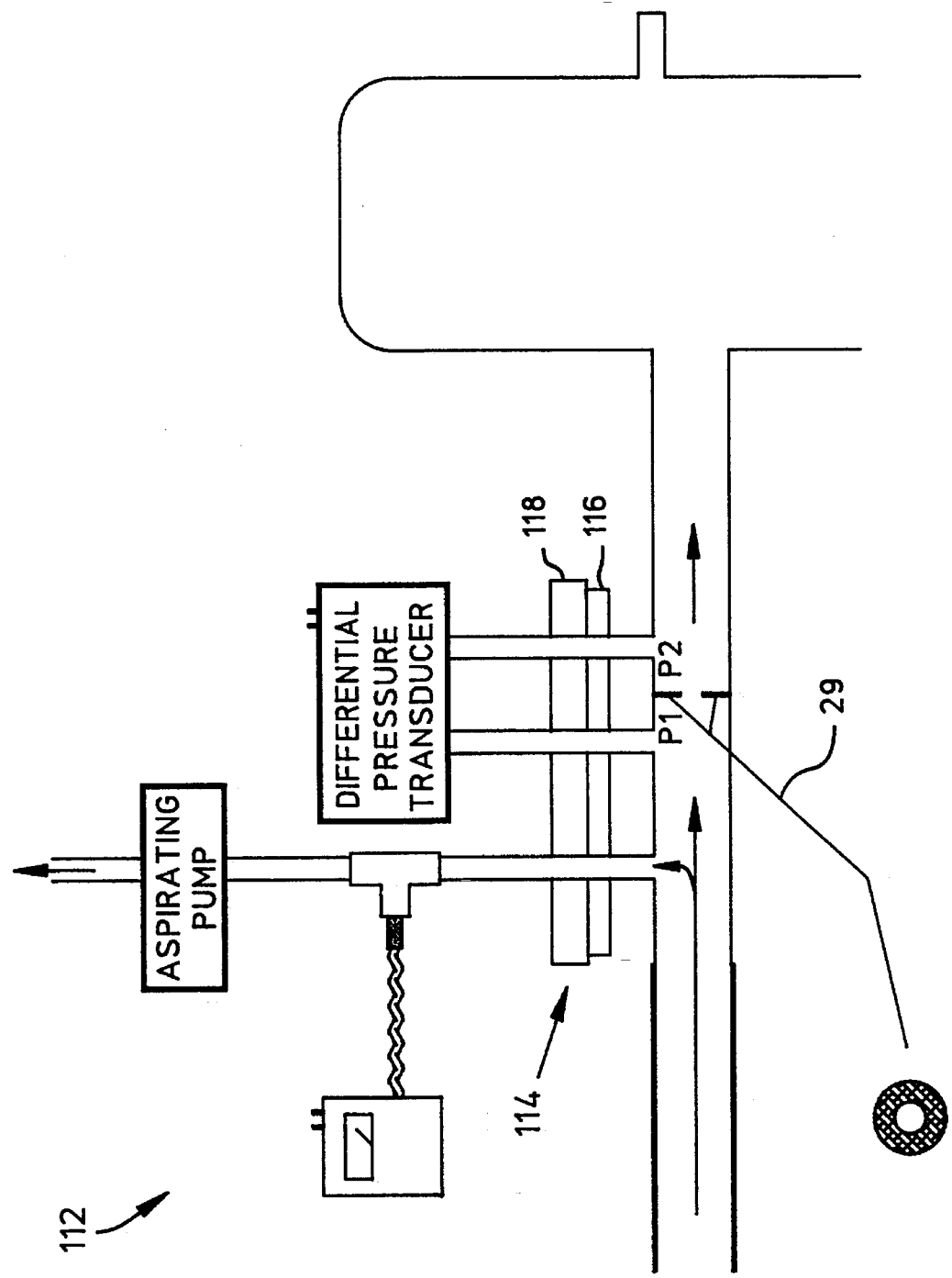
FIG. 5 shows another embodiment of the invention similar to the one described in FIG. 4, but modified in that a single connector has replaced the three individual luer lock connectors used to attach the tubings from the aspirating pump and differential pressure transducer to their corresponding orifices on the modified gas inlet of the oxygenator.

The present invention comprises a system for diagnosing oxygenator failure. The various embodiments of the present invention are described in FIGS. 4–11. For simplicity of illustration, only the present invention, the modified portion of the oxygenator, and a portion of the ventilating circuit is shown. It will be appreciated the remainder of the oxygenator ventilating circuit will be substantially identical to the one 32 shown in FIG. 2.

Referring now to FIG. 4, a portion of an oxygenator monitoring system 64 in accordance with the present invention is shown. In this embodiment, ventilating gas flows through a ventilating gas supply circuit 66 in polyvinyl chloride tubing 68 in the direction of the arrows shown and enters a modified gas inlet 70 of oxygenator 24. The polyvinyl chloride tubing 68 and modified gas inlet 70 are joined by a slip connection with tubing 68 sliding over the end of inlet 70. As the gas flows through modified gas inlet 70, a small amount of gas, approximately 100 ml per minute, is aspirated through the first of three orifices 72 by aspirating pump 74. The aspirated gas is pulled sequentially through the internal lumens of plastic connector 76, luer lock connection 78, connecting tubing 80, oxygen analyzer sensor housing 82, and the continuation of connecting tubing 80 to aspirating pump 74, where it is expelled to the atmosphere, or an evacuating system. As the aspirated ventilating gas flows through oxygen analyzer sensor housing 82, and passes oxygen analyzer sensor 84, polarographic oxygen analyzer 86 measures the oxygen concentration of the aspirated gas. The oxygen concentration is displayed at the oxygen analyzer 86, or at a remote display after relay of the information via output terminals 88.

The gas not aspirated through the first orifice 72 continues to flow through modified gas inlet 70. When the gas reaches a plate orifice flow resistor 90, pressure builds in the gas inlet because of the restriction to flow presented by the plate orifice flow resistor 90. After the gas passes through the orifice of the plate orifice flow resistor 90, pressure decreases. Therefore, a pressure differential is established on either side of the plate orifice flow resistor 90 and is represented in the diagram as pressures P1 and P2. P1 is transmitted through orifice 92, the internal lumens of plastic connector 94, luer lock connector 96, and high durometer pvc tubing 98 to differential pressure transducer 100. P2 is similarly transmitted through orifice 102, the internal lumens of plastic connector 104, luer lock connector 106, and high durometer pvc tubing 108 to the differential pressure transducer 100. Differential pressure transducer 100 reads the difference between P1 and P2. The greater P1 is relative to P2, the greater is the flow of gas through plate orifice flow resistor 90 and into oxygenator 24.

It will be appreciated that the differential pressure measurement can be used to calculate flow using well known standard techniques. Thus, differential pressure transducer 100 and associated electronics have been precalibrated, and can therefore associate the voltage differential created by the difference between P1 and P2 to a specific flow of gas passing through the gas inlet 70 and into oxygenator 24. The output terminals 110 relay the voltage differential of P1 and P2 to an amplifier and display screen.

Information about ventilating gas supply pressure, flow, and oxygen concentration may be displayed on a display 111 and interpreted by the operator of the system, or a dedicated diagnostic software or hardware system 113 may be implemented to interpret the data and provide a diagnosis.

Another embodiment of an oxygenator monitoring system 112 in accordance with the present invention is shown in FIG. 5. FIG. 5 is similar to FIG. 4 except that luer lock connectors 78, 96, 106 have been replaced with a single connector 114 which creates a tight seal between 76 and 80, 108 and 104, 94 and 98. The lower portion 116 of the new connector 114, mates with the upper portion 118. Upper portion 118 and lower portion 116 can be joined by threads, a slip and twist lock, or some other convenient manner so as to effectuate an airtight seal between the connectors 76, 94 and 104 and 80, 98 and 108, respectively.

Figure 6:
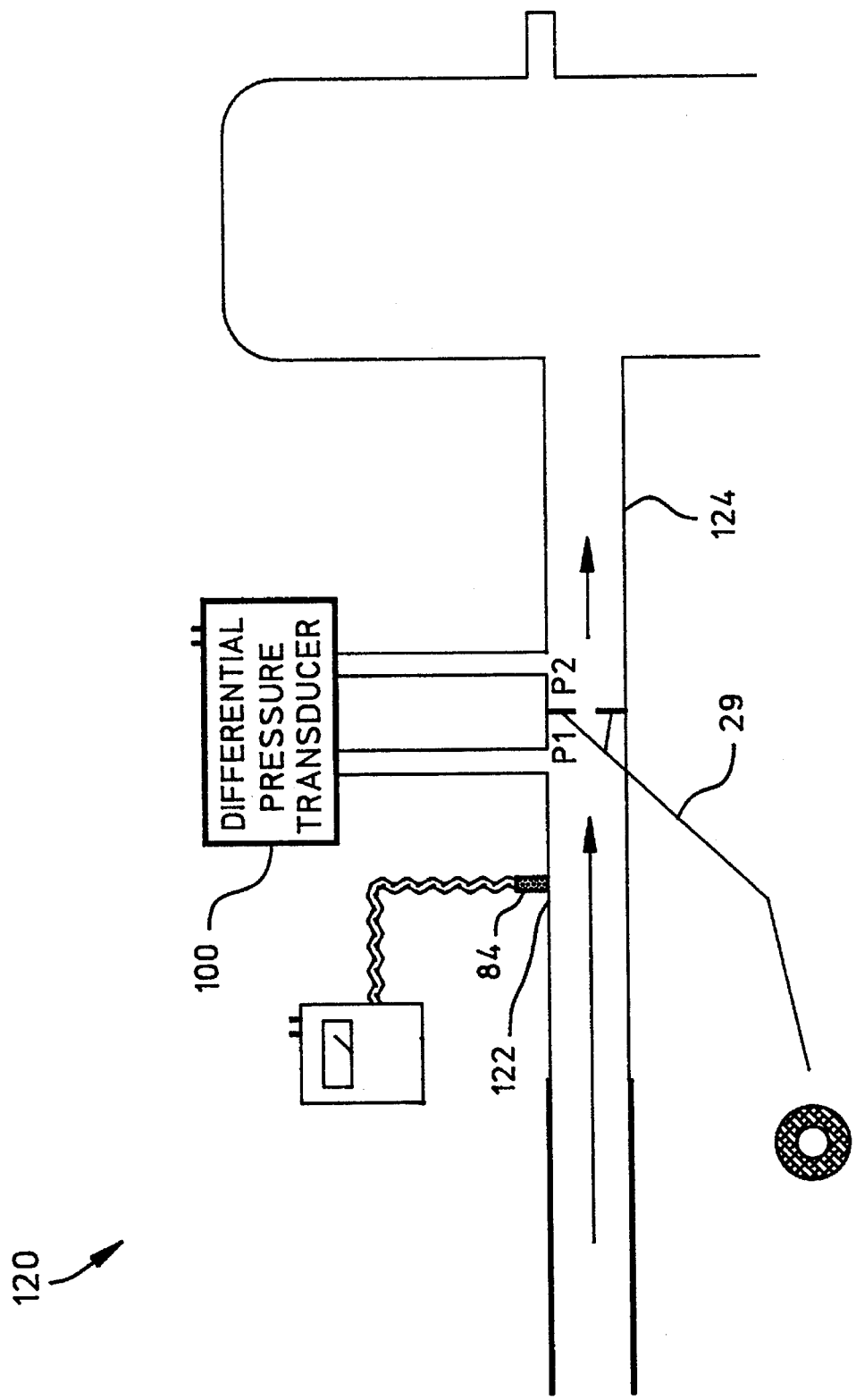
FIG. 6 shows a cross-sectional view of the gas inlet and oxygenator of one embodiment of the invention in which the gas inlet of the oxygenator has been modified with two orifices and connectors, and with a port that accepts the sensor portion of an oxygen analyzer.

FIG. 6 is similar to FIG. 4 except that in the oxygenator monitoring system 120 of this embodiment, orifice 72, plastic connector 76, luer lock connector 78, connecting tube 80, oxygen analyzer sensor housing 82, and aspirating pump 74 have been removed. Instead the oxygen analyzer sensor 84 fits directly into an orifice 122. in modified gas inlet 124. Orifice 122 is described in more detail in FIG. 11. In this embodiment, gas is no longer aspirated past oxygen analyzer sensor 84. Instead, oxygen analyzer sensor 84 reads directly the oxygen concentration of the ventilating gas flowing directly through modified gas inlet 124. One advantage of this embodiment is in the elimination of the aspirating pump resulting in less expensive hardware. However, now the system needs the valve shown in FIG. 11 to accept the oxygen sensor head.

Figure 7:
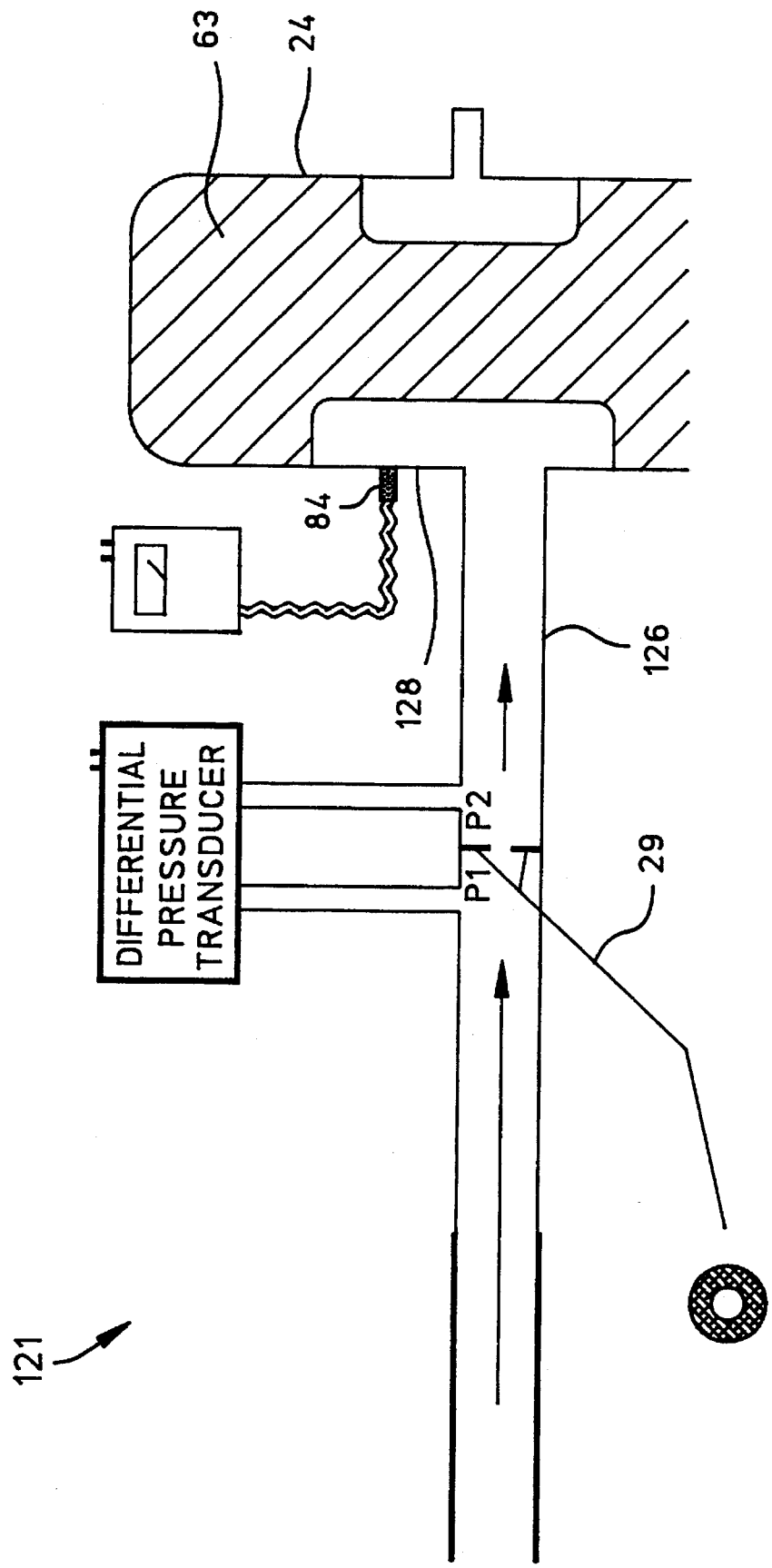
FIG. 7 shows a cross-sectional view of the gas inlet and oxygenator of another embodiment of the invention in which the gas inlet of the oxygenator is modified with two orifices and connectors, and where an oxygen analyzer is positioned directly in the oxygenator housing.

FIG. 7 shows an embodiment of the oxygenator monitoring system 121 which is similar to FIG. 6 except that orifice 122 is not present in modified gas inlet 126. An orifice 128 has been placed in the housing of oxygenator 24 and now holds oxygen analyzer sensor 84. All other function of this design are similar to FIG. 4. Note that the oxygen analyzer sensor 84 must be in an area of the oxygenator housing where it is exposed to gas that has not yet passed through the membrane 63 of oxygenator 24. One advantage of this version is that it allows for a compact gas inlet 126.

Figure 8:
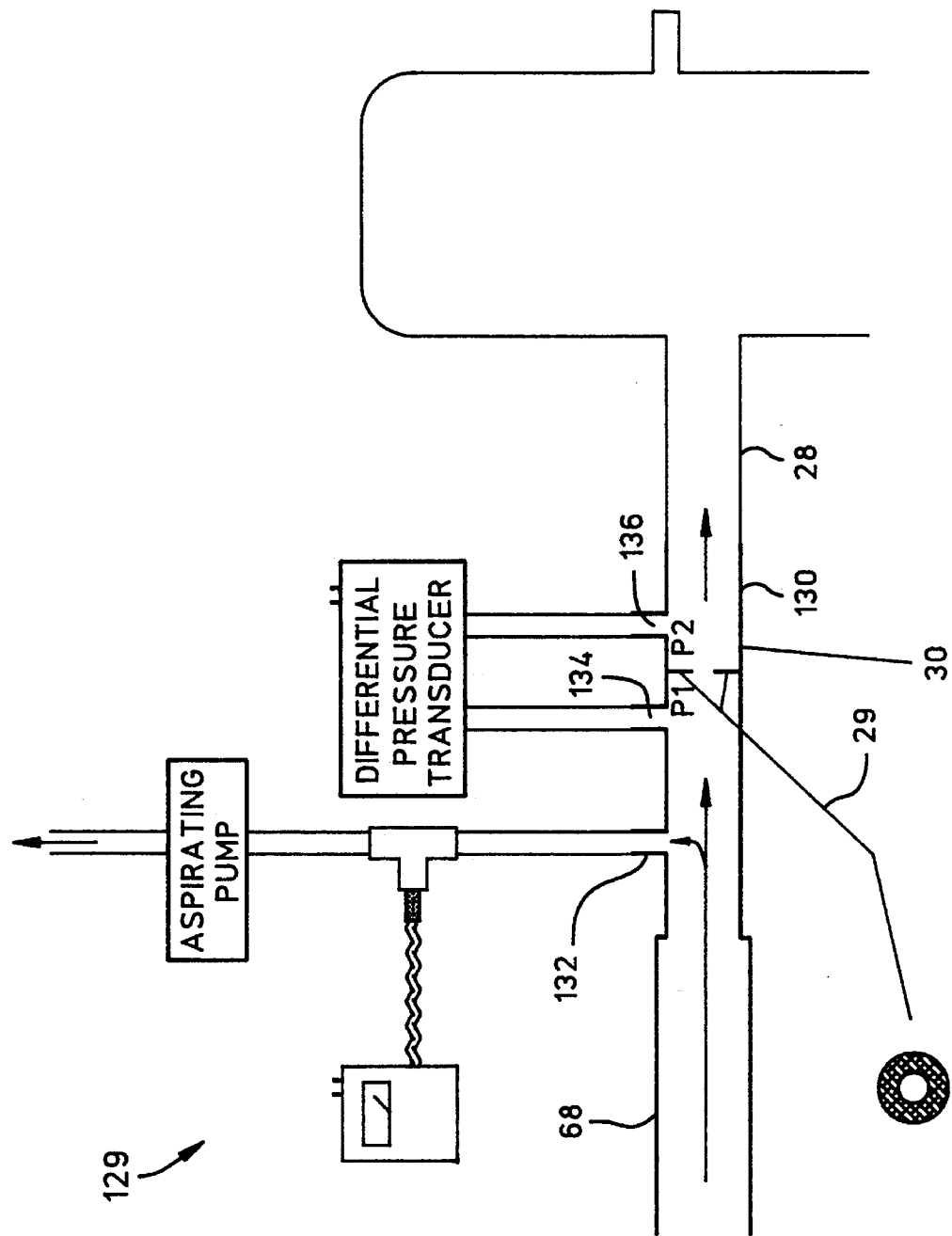
FIG. 8 shows a cross-sectional view of the gas inlet and oxygenator of one embodiment of the invention in which the gas inlet of the oxygenator has not been modified, but an attachment with three orifices and connectors is connected to the gas inlet.

FIG. 8 shows an embodiment of the oxygenator monitoring system 129 which is similar to FIG. 4 except that gas inlet 28 (shown in FIG. 2) has not been altered, and an attachment with three orifices 130 is temporarily or permanently affixed to gas inlet 28. In this embodiment, gas is aspirated through orifice 132 for oxygen analysis while orifices 134 and 136 transmit pressures P1 and P2, respectively, to differential pressure transducer 100 for flow measurement. One advantage of this embodiment is that it allows for placement in a non-modified gas inlet.

Figure 9:
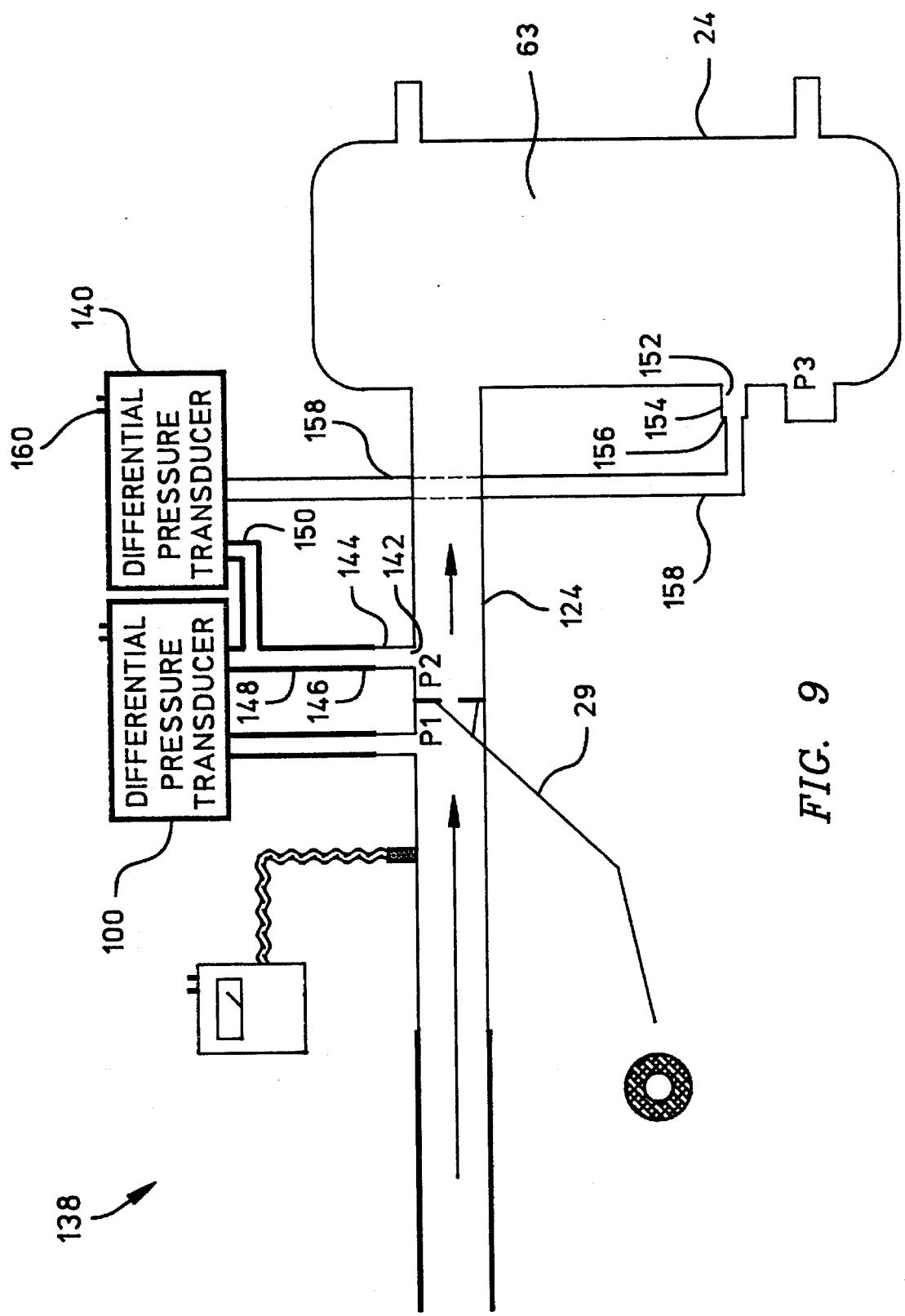
FIG. 9 shows a cross-sectional view of the gas inlet and oxygenator of an embodiment of the invention similar to the one described in FIG. 6, but with a second differential pressure transducer to measure the flow of gas through the oxygenator.

FIG. 9 shows an embodiment of the oxygenator monitoring system 138 which is similar to the one shown in FIG. 6 with the following exception. A second differential transducers 100 and 140 has been added which monitors pressure P2 and P3. P2 is transmitted through orifice 142, the internal lumens of connector 144, luer lock 146, high pressure tubings 148 and 150 to differential pressure transducer 140. P3 is transmitted through orifice 152, the internal lumens of connector 154, luer lock 156, high pressure tubing 158 to differential pressure transducer 140. The purpose of this arrangement is to provide a measurement of gas flow entering oxygenator 24 and perfusing the oxygenator 24 beyond modified gas inlet 124. This is accomplished by measuring the pressure drop from P2 to P3 which is created by resistance to gas flow created by the membrane 64 of oxygenator 24. This embodiment provides information necessary to diagnose not only an oxygenator failure, but a specific cause of oxygenator failure, that being a significant gas leak from the housing of oxygenator 24. Terminals 160 are available to relay information from differential pressure transducer 140 to a remote location.

Figure 10:
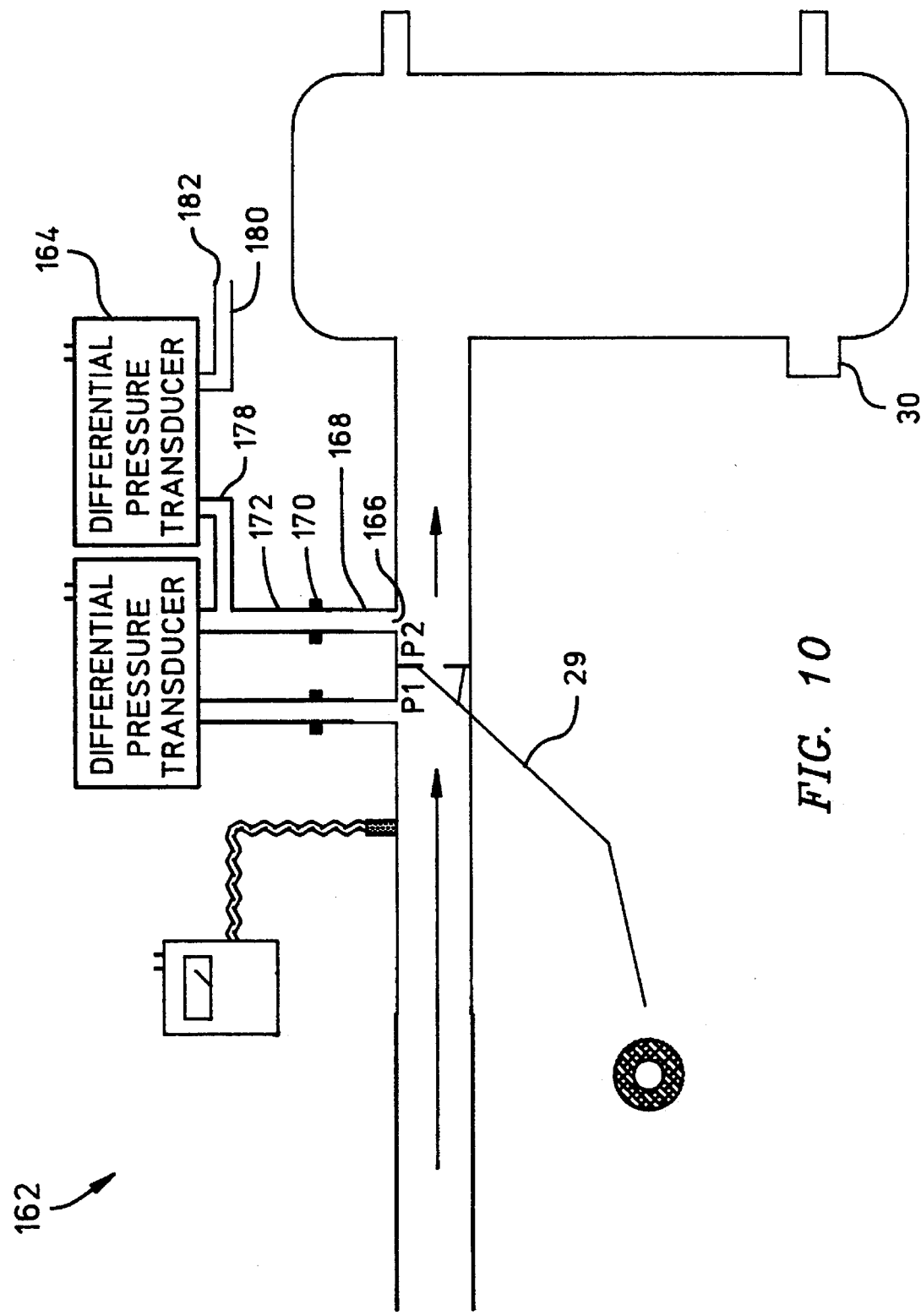
FIG. 10 shows a cross-sectional view of the gas inlet and oxygenator of one embodiment of the invention similar to the one described in FIG. 6, but having added a second differential pressure transducer that monitors pressure on the gas side of the oxygenator's membrane.

FIG. 10 shows an embodiment of the oxygenator monitoring system 162 which functions in a similar manner as the one shown in FIG. 6. However, a second differential pressure transducer measures P2 and atmospheric pressure. P2 is measured through orifice 166, the internal lumens of connector 168, luer lock 170, high pressure tubing 172 and 178. Atmospheric pressure is measured through the internal lumen of high pressure tubing 180 and orifice 182. Differential pressure transducer 164 compares P2 to atmospheric pressure. If an obstruction of gas outlet 30 occurs, P2 increases while atmospheric pressure does not change. Conversely, if a gas evacuation system malfunctions, P2 decreases while atmospheric pressure does not change. Therefore, this embodiment provides information necessary to diagnose not only an oxygenator failure, but a specific cause of oxygenator failure, that being obstruction of gas flow or subatmospheric pressure within the oxygenator.

FIG. 11 represents a port at orifice 122 (in FIG. 6) or 128 (in FIG. 7) for receiving the sensor of a polarographic oxygen analyzer. FIG. 11A shows a longitudinal cross-section of the valve 184 and the port 186 with the valve in the closed position. Occlusion plate 188 rests against the thickened portion of wall 190 with spring 192 holding occlusion plate 188 in a closed position so no gas can escape. Windows 194 allow passage of gas into the central portion of the valve.

The valve depicted in 11A, 11B and 11C can easily be fabricated by companies in the business of manufacturing injection molded components or valves.

FIG. 11B shows the same longitudinal cross-section as FIG. 11A with a polarographic oxygen analyzer sensor 84 inserted into valve. When seated, occlusion plate 188 is displaced interiorly. The tip 196 of sensor 84 rests by the windows 194 and is thereby exposed to the gas. A membrane 198 which is permeable to the ventilatory gas, but impermeable to microbial agents lines the windows 194.

FIG. 11C shows a top view of the port 186 without the polarographic oxygen analyzer sensor inserted. Occlusion plate 188 can be seen through port 186.

In another alternative embodiment of the present invention, the oxygenator monitoring system is configured as the system in FIG. 4, with the differential pressure transducer 100 removed, to provide for the oxygen analysis of an aspirated (suction-sampled) gas sample only. Flow is not measured in this embodiment. In this embodiment a sample of the ventilating gas supply is removed from the oxygenator gas inlet port 70 by a small pump 74 and sampled by an oxygen analyzer 84 and 86 placed a distance from the oxygenator housing. (Typical samples may be in the range of 50 ml to 250 ml per minute.)

The use of the aspirating oxygen analyzer in this manner (without a flow sensor) permits the differentiation of oxygenator failure from either a complete loss of oxygen in the ventilating gas supply, or abnormal oxygen concentrations of the ventilating gas. It would not differentiate oxygenator failure from a reduction of gas flow if said gas flow is not accompanied by an alteration of oxygen concentration. If the complete loss of ventilating gas resulted from a disconnection on the ventilating gas circuit, room air will be aspirated by aspirating pump 74 through that circuit defect. If all ventilating gas flow is lost, without a disconnection, aspirating pump 74 will pull oxygen depleted gas back from the oxygenator. In contrast, an oxygen analyzer (not an aspirating arrangement) placed in the ventilating gas circuit (50, FIG. 2) will not detect the complete loss of ventilating gas. This occurs since the oxygen sensor 52 to sits in a bath of stagnant oxygen-rich ventilating gas which remains in the ventilating gas circuit but is not flowing into the oxygenator.

Since the aspirating oxygen analyzer cannot detect a reduction in ventilating gas flow (if the flow is still greater than a very small amount), it is not as effective as the combination of an oxygen analyzer and flow sensor. The advantage of using the aspirating oxygen sensor alone (unaccompanied by a flow sensor) as opposed to current technology is that it is capable of differentiating oxygenator failure from the catastrophic problems of complete loss of ventilating gas or unrecognized low oxygen concentration, and is less expensive to implement than a flow sensor/oxygen analyzer.

FIG. 12 shows a fault diagnosis matrix for ventilating gas supplied to oxygenator. Three sensor arrangements and four faults are shown. A check mark indicates that the sensor when used alone is capable of detecting that fault. For example, "Disconnection" can be detected by either an "aspirating oxygen sensor" or by "Flow". The "passive oxygen sensor" can only detect "Low $O_2$ concentration without cessation of".

From the forgoing it can be seen that the present invention provides the necessary information for diagnosing oxygenator malfunction. The health and well-being of a patient on cardiopulmonary bypass is dependant on the appropriate function of an oxygenator. Despite the numerous published articles that cite a variety of problems with oxygenator function, no monitoring device or system has been invented that is capable of evaluating oxygenator function. Consequently, numerous patients have suffered adverse outcomes during cardiopulmonary bypass. This invention is unique and effective, and answers a long standing clinical need.

During cardiopulmonary bypass, if a problem in oxygenation becomes apparent, correction of the initiating cause becomes critical. Quick diagnosis regarding the cause of this problem, be it an oxygenator failure or some other malfunction, is presently impossible. Primarily, this invention offers the benefit of providing continuous, realtime information needed to differentiate oxygenator failure from other causes of inadequate gas exchange by the oxygenator during cardiopulmonary bypass. Additionally, this invention has the capability to differentiate between various types of ventilating gas supply problems. Finally, this invention if appropriately configured (FIGS. 9 and 10) also has the potential to differentiate specific, types of oxygenator malfunction.

Accordingly, the reader will also see that this invention provides constant measurement of pressure on the gas side of the membrane in the oxygenator. Obstruction of the gas outlet of the oxygenator will increase pressure on the gas side of the membrane and can force gas bubbles through the membrane and into the blood. Such a situation can result in stroke, heart attack and/or other body organ failures. Similarly, a negative pressure created on the gas side of the membrane will interfere with the normal transfer of gas through the membrane which can result in hypoxemia.

Although the descriptions above contain many specificities, these should not be construed as limiting the scope of the invention but as merely providing illustrations of some of the presently preferred embodiments of this invention. For example, the oxygen analyzer need not be of the polarographic type. Also, the flow restrictor need not be of a plate orifice design in order to determine flow; and the method by which flow is determined need not be by the principle of pneumotachography since numerous other methods are available.

Those skilled in the art can appreciate that other advantages can be obtained from the use of this invention and that modification may be made without departing from the true spirit of the invention after studying the specification, drawings and following claims.

What is claimed:

1. In an oxygenator system including an oxygenator having a ventilating gas inlet and oxygenator ventilating circuit means for supplying ventilating gas to said ventilating gas inlet of said oxygenator, said oxygenator for receiving and oxygenating a patient's blood, apparatus for assessing oxygen function comprising:

oxygen concentration measurement means, coupled between said oxygenator ventilating circuit means and said ventilating gas inlet of said oxygenator, for measuring the oxygen concentration of said ventilating gas at said ventilating gas inlet of said oxygenator; and flow measuring means, coupled to said oxygenator system at or immediately adjacent to said ventilating gas inlet of said oxygenator, for measuring the flow of said ventilating gas supplied to said ventilating gas inlet of said oxygenator.

2. The apparatus of claim 1 further comprising:

display means, coupled to said oxygen concentration measuring means and said flow measuring means, for displaying the oxygen concentration and the flow of said ventilating gas at said ventilating gas inlet.

3. The apparatus of claim 1 wherein said oxygenator includes a housing and said oxygen concentration measurement means measures the oxygen concentration within said oxygenator housing.

4. The apparatus of claim 3 wherein said oxygen concentration measurement means is disposed at a location within said oxygenator housing where gas exchange has not yet occurred between said ventilating gas and the patient's blood.

5. The apparatus of claim 1 wherein said oxygen concentration measurement means is disposed within the ventilating gas inlet of said oxygenator.

6. The apparatus of claim 1 further comprising:

means for removing gas from said ventilating gas inlet of said oxygenator, wherein said oxygenator concentration measurement means measures the oxygen concentration of said ventilating gas removed from said ventilating gas inlet.

7. The apparatus of claim 1 further comprising a port which communicates between the external environment and the internal lumen of said ventilating gas inlet of said oxygenator.

8. The system of claim 1 further comprising:

diagnostic means, coupled to said oxygen concentration measuring means and said flow measuring means, for diagnosing oxygenator malfunctions.

9. Apparatus for assessing oxygenator function comprising:

an oxygenator, having a ventilating gas inlet and a ventilating gas outlet, for receiving and oxygenating a patient's blood;

oxygenator ventilating circuit means, coupled to said ventilating gas inlet of said oxygenator, for supplying ventilating gas to said oxygenator;

oxygen concentration measurement means, coupled between said oxygenator ventilating circuit means and said ventilating gas inlet and located adjacent to said ventilating gas inlet, for measuring the oxygen concentration of said ventilating gas at said ventilating gas inlet of said oxygenator; and flow measuring means, associated with said vetilating gas inlet and said ventilating gas outlet of said oxygenator, for measuring the flow of said ventilating gas perfusing said oxygenator.

10. The apparatus of claim 9 wherein said oxygenator includes a housing means and said oxygen concentration measurement means measures the oxygen concentration of the ventilating gas within said oxygenator housing adjacent said ventilating as inlet.

11. The apparatus of claim 10 wherein said oxygen concentration measurement means is disposed in a location within said oxygenator housing where gas exchange has not yet occurred between said ventilating gas and the patient's blood.

12. The apparatus of claim 9 wherein said flow measuring means includes a differential pressure transducer having first and second inputs coupled to said ventilating gas inlet and said ventilating gas outlet, respectively, of said oxygenator.

13. The apparatus of claim 9 further comprising means for removing gas from said oxygenator gas inlet, wherein said oxygen concentration measurement means analyzes the oxygen concentration of said ventilating gas removed from said ventilating gas inlet.

14. The apparatus of claim 9 wherein said flow measuring means includes a differential pressure transducer having first and second inputs coupled to said ventilating gas inlet on opposite sides of a flow resistor.

15. Apparatus for assessing oxygenator function comprising:

an oxygenator having an inlet for receiving ventilating gas;

oxygen concentration measurement means, associated with said inlet, for measuring the oxygen concentration of said ventilating gas at said inlet;

flow measuring means, associated with said inlet, for measuring the flow of said ventilating gas at said inlet of said oxygenator; and means, associated with said inlet, for measuring the difference between atmospheric pressure and the pressure of gas at said inlet.

16. The apparatus of claim 15 wherein said flow measuring means further comprises an orifice positioned within said oxygenator gas inlet, and a differential pressure transducer means for measuring the pressure differential between the gas in said inlet on opposite sides of said orifice.

17. A diagnostic system for assessing the function of an oxygenator which receives and oxygenates a patient's blood, said diagnostic system comprising:

oxygenator ventilating circuit means for supplying ventilating gas to said oxygenator;

oxygen concentration measurement means, coupled between said oxygenator ventilating circuit means and a ventilating gas inlet of said oxygenator, for measuring the oxygen concentration of said ventilating gas supplied to said ventilating gas inlet of said oxygenator;

flow measuring means, coupled between said oxygenator ventilating circuit means and said ventilating gas inlet of said oxygenator, for measuring the flow of ventilating gas at said ventilating gas inlet: and diagnostic means, coupled to said oxygen concentration measuring means and said flow measuring means, for diagnosing oxygenator malfunctions.

* * * * *